United States Patent
Ogura et al.

(10) Patent No.: US 9,186,117 B2
(45) Date of Patent: Nov. 17, 2015

(54) X-RAY IMAGING APPARATUS

(71) Applicant: CANON KABUSHIKI KAISHA, Tokyo (JP)

(72) Inventors: Takashi Ogura, Tokyo (JP); Jun Murata, Utsunomiya (JP); Hideki Hayashi, Kiyose (JP); Yusuke Hokari, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 65 days.

(21) Appl. No.: 14/132,804

(22) Filed: Dec. 18, 2013

(65) Prior Publication Data

US 2014/0177797 A1  Jun. 26, 2014

(30) Foreign Application Priority Data

Dec. 21, 2012  (JP) ................................. 2012-279482

(51) Int. Cl.
  *H05G 1/02* (2006.01)
  *A61B 6/00* (2006.01)
  *A61B 6/06* (2006.01)

(52) U.S. Cl.
  CPC ............ *A61B 6/4405* (2013.01); *A61B 6/4429* (2013.01); *A61B 6/54* (2013.01); *A61B 6/06* (2013.01); *A61B 6/4494* (2013.01); *A61B 6/548* (2013.01)

(58) Field of Classification Search
  CPC ..... A61B 6/032; A61B 6/4405; A61B 6/4441; A61B 6/4429
  USPC ............................................. 378/62, 193–197
  See application file for complete search history.

(56) References Cited

U.S. PATENT DOCUMENTS

| 4,495,635 A | * | 1/1985 | Dobbs ............................. 378/56 |
| 6,102,567 A | * | 8/2000 | Cabral et al. ................... 378/197 |
| 2012/0069960 A1 | * | 3/2012 | Kitagawa et al. ............... 378/41 |
| 2012/0076264 A1 | * | 3/2012 | Ohta et al. ...................... 378/62 |

FOREIGN PATENT DOCUMENTS

| JP | 2011056170 A | 3/2011 |
| JP | 2011136028 A | 7/2011 |

* cited by examiner

*Primary Examiner* — Courtney Thomas
(74) *Attorney, Agent, or Firm* — Canon USA Inc., IP Division

(57) ABSTRACT

An X-ray imaging apparatus includes an X-ray generating unit, an X-ray image receiving unit, a control unit, and an arm unit. The X-ray generating unit radiates X-rays. The X-ray image receiving unit receives X-rays radiated by the X-ray generating unit. The control unit controls the X-ray generating unit and the X-ray image receiving unit. The arm unit is configured to extend so as to position the X-ray generating unit and the control unit above the X-ray image receiving unit and to retract in the case of transportation.

9 Claims, 5 Drawing Sheets

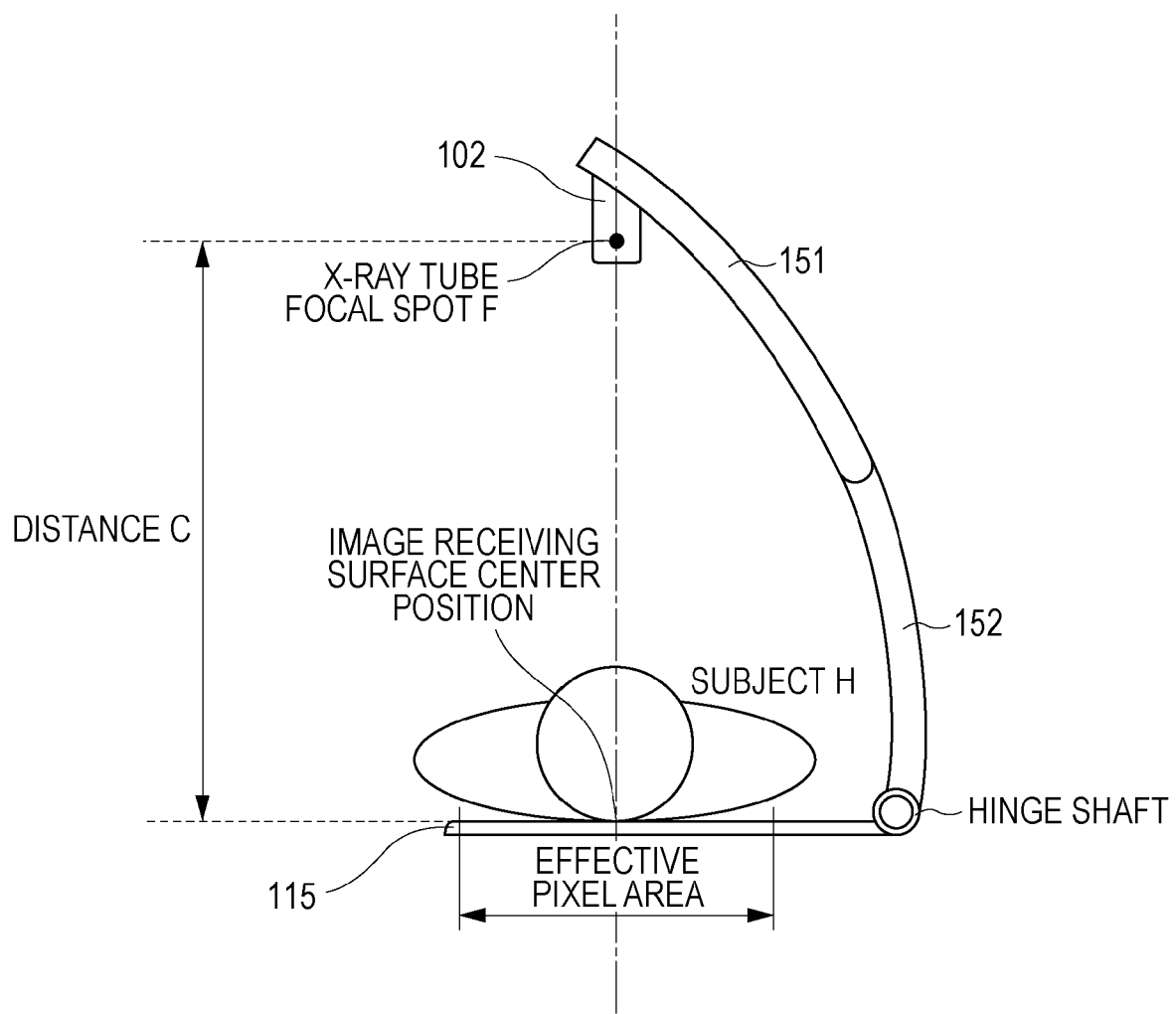

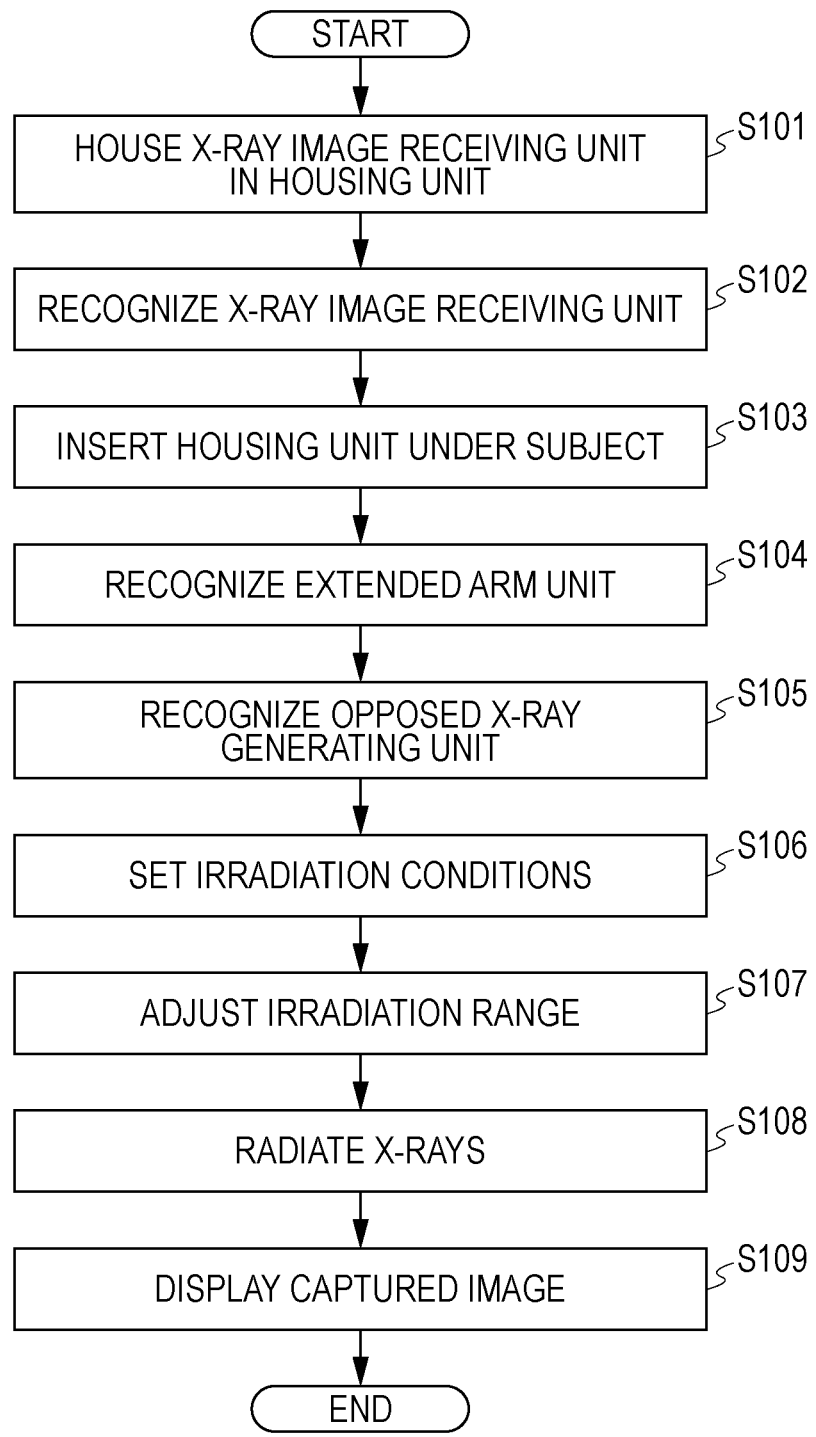

X-RAY IMAGING APPARATUS

BACKGROUND OF THE INVENTION

1. Field of the Invention

The present invention relates to an X-ray imaging apparatus including an X-ray tube, an X-ray image receiving unit, a control unit that controls the X-ray tube and the X-ray image receiving unit, and an arm unit that extends above the X-ray image receiving unit.

2. Description of Related Art

In recent years, an X-ray imaging apparatus used for medical diagnosis or the like has become more portable due to reduction in the size and weight of an X-ray generator including an X-ray tube and has come into use in an emergency or home medical care.

Japanese Patent Laid-Open No. 2011-56170 discloses a technique in which an X-ray tube is used by being suspended vertically above an examination region of a subject by a holder that is capable of being assembled/disassembled. In an X-ray imaging apparatus as disclosed in Japanese Patent Laid-Open No. 2011-56170, however, the holder has to be assembled and installed before X-ray imaging is performed, which requires time and effort and is therefore an issue. Furthermore, since the X-ray tube and the holder are separated from each other, portability itself is poor, which is also an issue.

Japanese Patent Laid-Open No. 2011-136028 discloses a structure in which an arm unit to which an X-ray tube is attached is fixed with a clip or a sucking disc. With the structure described in Japanese Patent Laid-Open No. 2011-136028, reduction in the size of the entire apparatus including the arm unit may be achieved. However, the positional relationship between the X-ray tube and an X-ray image receiving unit has to be adjusted with a rotary encoder and a motor provided in the arm unit before imaging. Therefore the structure described in Japanese Patent Laid-Open No. 2011-136028 has an issue in that prompt X-ray imaging is difficult. Furthermore, with fixation using a clip or a sucking disc, it is difficult to maintain a certain level of strength, which is also an issue.

SUMMARY OF THE INVENTION

Embodiments of the present invention disclose an X-ray imaging apparatus in which installability, portability, and operability are increased. To address the shortcomings of the related art described above, an X-ray imaging apparatus according to an aspect of the present invention includes an X-ray generating unit, an X-ray image receiving unit, a control unit, and an arm unit. The X-ray generating unit radiates X-rays. The X-ray image receiving unit receives X-rays radiated by the X-ray generating unit. The control unit controls the X-ray generating unit and the X-ray image receiving unit. The arm unit is capable of extending so as to position the X-ray generating unit and the control unit above the X-ray image receiving unit and being retracted in the case of transportation. The arm unit that fixes an X-ray tube and the control unit in place is capable of being retracted and therefore portability of the X-ray imaging apparatus may be increased. Furthermore, the arm unit that fixes the X-ray tube and the control unit in place is capable of being extended so as to dispose the X-ray tube and the control unit above the X-ray image receiving unit and therefore positioning of the irradiation field of an X-ray source becomes unnecessary. Advantageously, ease of installation and operability of the X-ray imaging apparatus are improved.

Further features of the present invention will become apparent from the following description of exemplary embodiments with reference to the attached drawings.

BRIEF DESCRIPTION OF THE DRAWINGS

FIG. 3 is a two-dimensional diagram (side view) schematically illustrating a relationship among an X-ray generating unit, an X-ray image receiving unit, a control unit, and an arm unit of the X-ray imaging apparatus.

FIG. 5 is a flowchart illustrating an example of processing relating to the X-ray imaging apparatus according to an exemplary embodiment of the present invention.

DESCRIPTION OF THE EMBODIMENTS

Figure 1:
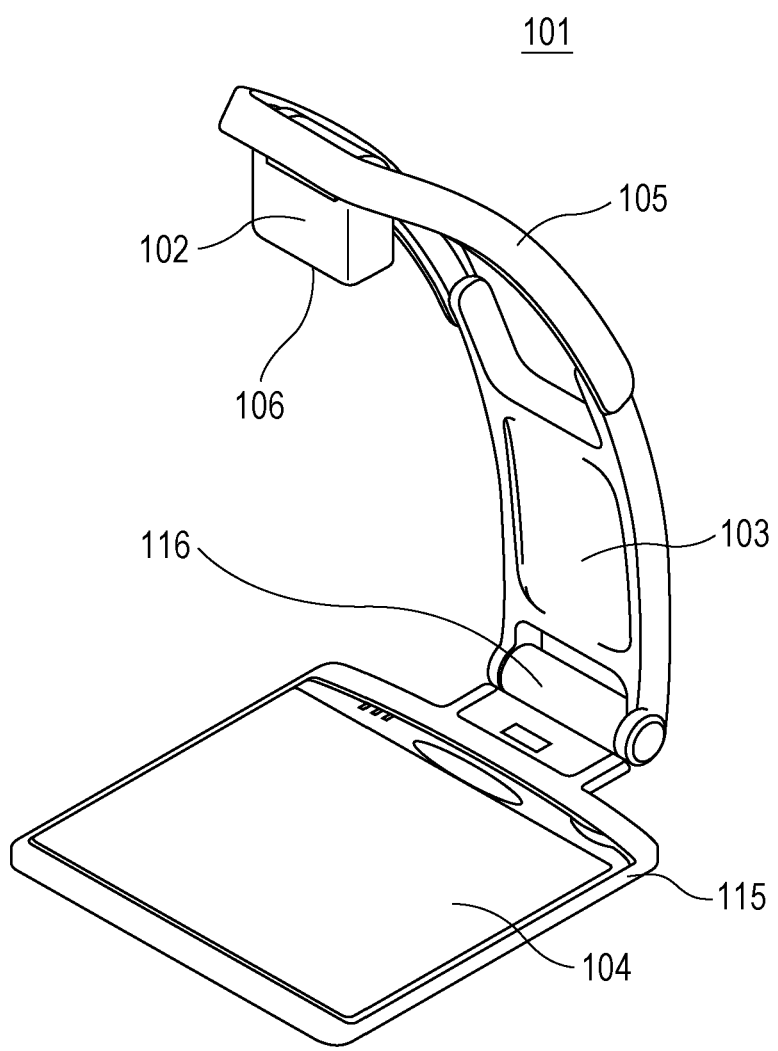
FIG. 1 is a perspective view schematically illustrating an X-ray imaging apparatus according to an exemplary embodiment of the present invention.

Several aspects of the present invention are described below in detail with reference to the drawings. In the drawings like numbered elements represent like parts, structures or functions throughout.

First Exemplary Embodiment

Figure 2:
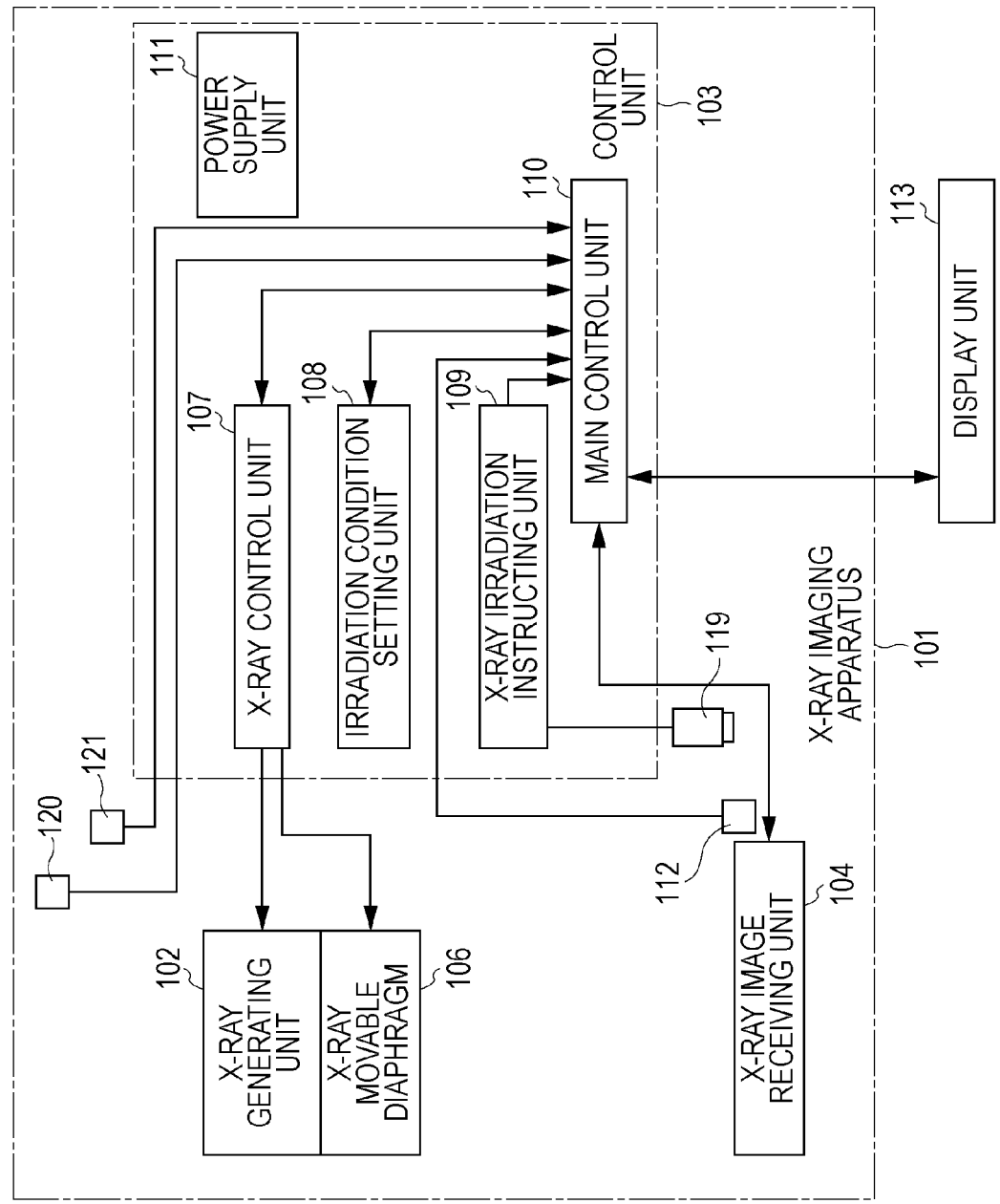
FIG. 2 is a block diagram schematically illustrating a system configuration of the X-ray imaging apparatus.

FIG. 1 is a diagram schematically illustrating a structure of a principal part of an X-ray imaging apparatus 101 according to an exemplary embodiment of the present invention. FIG. 2 is a block diagram illustrating a system configuration of the X-ray imaging apparatus 101 according to the exemplary embodiment of the present invention.

As illustrated in FIGS. 1 and 2, the X-ray imaging apparatus 101 includes an X-ray generating unit 102, a control unit 103, an X-ray image receiving unit 104, and an arm unit 105. The X-ray generating unit 102, the control unit 103, and a housing unit 115 that contains the X-ray image receiving unit 104 are fixed in place by the arm unit 105.

When the X-ray generating unit 102 receives an X-ray generation signal (described below) from an X-ray control unit 107 of the control unit 103 described below, the X-ray generating unit 102 generates and radiates X-rays toward a subject H (shown in FIG. 3). The X-ray generating unit 102 has an X-ray tube (not illustrated) that generates X-rays, a high voltage generating unit (not illustrated) for driving the X-ray tube, and an X-ray movable diaphragm 106 that restricts an irradiation range of X-rays.

The X-ray tube radiates thermoelectrons emitted from a filament heated to a high temperature to an X-ray target made of tungsten or molybdenum, for example, to thereby generate X-rays. The X-ray tube and the high voltage generating unit are disposed in the interior of a container included in the X-ray generating unit 102. The interior of the container is filled with insulating oil.

The X-ray movable diaphragm 106 is provided in an irradiation port of the X-ray generating unit 102. The X-ray movable diaphragm 106 is a mechanical structure used to restrict the irradiation range of X-rays radiated from the X-ray tube and is used for preventing or reducing exposure of a region other than a diagnosis target region of the subject H. The X-ray movable diaphragm 106 is generally of a movable type. An operator or the like is capable of adjusting the irradiation range of X-rays by, for example, moving lead blades provided in the X-ray movable diaphragm 106 while checking the irradiation range using a lamp provided in the X-ray movable diaphragm 106. The X-ray movable diaphragm 106 is also capable of automatically adjusting the irradiation range of X-rays (which is described later).

The X-ray image receiving unit 104 is held in the housing unit 115 of a tray shape having an upper opening as illustrated in FIG. 1 or the housing unit 115 of a bag shape having a side opening (not illustrated). The housing unit 115 and the arm unit 105 are joined to each other by a joint 116 having a bending mechanism like a hinge and therefore are pivotable on the joint 116.

The X-ray image receiving unit 104 has an image receiving surface and is housed in the housing unit 115 such that the image receiving surface faces the X-ray generating unit 102. The X-ray image receiving unit 104 detects X-rays radiated from the X-ray generating unit 102 and receives an X-ray image on the image receiving surface. As the X-ray image receiving unit 104, a flat panel detector (FPD) sensor, a computed radiography (CR) cassette, a film cassette, or the like, various types of which are available, is used.

The size of the FPD sensor or the like as the X-ray image receiving unit 104 includes a half cut size, a large quarter cut size, a quarter cut size, and the like. The half cut size has short sides of 383.5±1.0 mm and long sides of 459.5±1.0 mm. The large quarter cut size has short sides of 307.5±1.0 mm and long sides of 383.5±1.0 mm. The quarter cut size has short sides of 281.5±1.0 mm and long sides of 332.5±1.0 mm. These sizes are defined in Japanese Industrial Standards (JIS). The orientation of the FPD sensor or the like includes a portrait orientation in a case where the FPD sensor or the like is used longitudinally, and a landscape orientation in a case where the FPD sensor or the like is used laterally in relation to the subject H. The orientation is selected appropriately in accordance with the region to be imaged and the purpose of imaging.

The housing unit 115 is capable of housing any one of an FPD sensor, a CR cassette, or a film cassette, which serves as the X-ray image receiving unit 104. Furthermore, the size and orientation of the X-ray image receiving unit 104 that is housed in the housing unit 115 is selectable as desired. That is, the housing unit 115 is capable of housing an FPD sensor or the like of any size described above and the orientation (portrait or landscape) of an FPD sensor or the like that is housed in the housing unit 115 is selectable as desired.

At least the surface side, on which X-rays are incident, of the housing unit 115 of a bag shape having a side opening (the side on which the image receiving surface of the X-ray image receiving unit 104 is positioned) is formed of an X-ray transmitting material such as a synthetic resin material or carbon fiber reinforced plastic (CFRP) of various types. An FPD sensor, a CR cassette, or a film cassette, which serves as the X-ray image receiving unit 104, is capable of being inserted into and removed from an opening of the housing unit 115. The height of the opening is made larger than 15 mm, which is the thickness of the FPD sensor or the like. After the housing unit 115 in which the X-ray image receiving unit 104 is housed is inserted under a lying subject H, the X-ray generating unit 102 is allowed to radiate X-rays toward the subject H.

An X-ray image receiving unit recognition unit 112 is provided in the interior or on the bottom of the housing unit 115. The X-ray image receiving unit recognition unit 112 recognizes whether or not the X-ray image receiving unit 104 is housed (mounted) in the housing unit 115 and, in the case where the X-ray image receiving unit 104 is housed, recognizes the kind of the X-ray image receiving unit 104 (for example, an FPD sensor, a CR cassette, or a film cassette) and the size and orientation of the X-ray image receiving unit 104. For example, identification information is provided on the exterior of the X-ray image receiving unit 104 and the X-ray image receiving unit recognition unit 112 reads the identification information and performs the above recognition processing. As the identification information provided on the exterior of the X-ray image receiving unit 104, a one-dimensional code, a two-dimensional code, a radio frequency identification (RFID) tag, or the like of various types may be used. The X-ray image receiving unit recognition unit 112 includes various kinds of predetermined readers, reads the identification information provided on the exterior of the X-ray image receiving unit 104, and performs recognition processing.

The X-ray image receiving unit recognition unit 112 generates a recognition signal from the result of the recognition processing and transmits the generated recognition signal to an irradiation condition setting unit 108. The recognition signal includes information on whether or not the X-ray image receiving unit 104 is housed and the kind (an FPD sensor, a CR cassette, or a film cassette), the size, and the mounting orientation of the X-ray image receiving unit 104.

Note that, in the case where the X-ray image receiving unit 104 housed in the housing unit 115 is replaced after the X-ray generating unit 102 has radiated X-rays, the X-ray image receiving unit recognition unit 112 performs again the recognition processing on the X-ray image receiving unit 104 and updates the recognition signal. The X-ray image receiving unit recognition unit 112 updates the recognition signal to thereby recognize whether or not the X-ray image receiving unit 104 has been replaced. In the case where the X-ray image receiving unit 104 is recognized to be a CR cassette or a film cassette (that is, the one that is replaced each time imaging is performed) and the recognition signal is not updated, the control unit 103 restricts further X-ray irradiation. More specifically, in the case where the X-ray image receiving unit recognition unit 112 does not update the recognition signal, the X-ray image receiving unit recognition unit 112 determines that the X-ray image receiving unit 104 has not been replaced. Accordingly, double irradiation of the same CR cassette or film cassette with X-rays is prevented from occurring.

The control unit 103 includes the X-ray control unit 107, the irradiation condition setting unit 108, an X-ray irradiation instructing unit 109, a main control unit 110, and a power supply unit 111.

The irradiation condition setting unit 108 is capable of setting X-ray irradiation conditions in accordance with an operation performed by an operator. For example, a touch panel is disposed on an exterior portion of the control unit 103 and an operator performs an operation for setting X-ray irradiation conditions. The X-ray irradiation conditions include an X-ray tube voltage, an X-ray tube current, X-ray irradiation time, and the like. Note that the irradiation condition setting unit 108 is capable of setting the X-ray irradiation conditions on the basis of the recognition signal received from the X-ray image receiving unit recognition unit 112, setting the X-ray irradiation conditions at recommended values, or setting the X-ray irradiation conditions automatically at predetermined values. The main control unit 110 calculates the dose and the like of X-rays on the basis of the values of the X-ray irradiation conditions set by the irradiation condition setting unit 108, generates an irradiation condition signal, and transmits the generated irradiation condition signal to the X-ray control unit 107. The irradiation condition signal includes information on the X-ray irradiation conditions such as the dose of X-rays.

An operation unit 119 is connected to (or provided in) the X-ray irradiation instructing unit 109. The operation unit 119 includes a button or the like for operating the X-ray irradiation instructing unit 109. The X-ray irradiation instructing unit 109 and the operation unit 119 transmit to the main control unit 110 a signal (hereinafter referred to as an "X-ray irradiation instruction signal") for giving an instruction to radiate X-rays in response to an operation performed by an operator. A dead-man-type X-ray irradiation switch is used with the X-ray irradiation instructing unit 109 and the operation unit 119. More specifically, when the X-ray irradiation instructing unit 109 detects pressing of a button provided in the operation unit 119 by an operator, the X-ray irradiation instructing unit 109 transmits an X-ray irradiation instruction signal to the X-ray control unit 107. When the X-ray irradiation instructing unit 109 detects releasing of the button provided in the operation unit 119, the X-ray irradiation instructing unit 109 instantaneously transmits to the main control unit 110 a signal (hereinafter referred to as an "X-ray irradiation stop instruction signal") for giving an instruction to stop the X-ray irradiation.

Note that the X-ray irradiation instructing unit 109 and the operation unit 119 may be configured such that a remote control switch that allows an operator to perform a remote operation is used. For example, as the X-ray irradiation instructing unit 109 and the operation unit 119, a configuration including a remote switch for generating infrared signals and an infrared receiving unit provided in the exterior portion of the control unit 103 may be used. When the X-ray irradiation instructing unit 109 detects operation of the button provided in the operation unit 119 by an operator, the X-ray irradiation instructing unit 109 transmits the X-ray irradiation instruction signal to the main control unit 110. When the X-ray irradiation instructing unit 109 detects releasing of the button by an operator, the X-ray irradiation instructing unit 109 instantaneously transmits the X-ray irradiation stop instruction signal to the main control unit 110. Note that the X-ray irradiation instructing unit 109 and the operation unit 119 may be configured so as to communicate with the main control unit 110 in accordance with the radio system based on the IEEE 802.11 standard that is widely used in wireless LANs for PCs.

When the X-ray control unit 107 receives the irradiation condition signal from the irradiation condition setting unit 108 and the X-ray irradiation instruction signal from the X-ray irradiation instructing unit 109 via the main control unit 110, the X-ray control unit 107 generates an X-ray generation signal on the basis of the received signals. The X-ray control unit 107 transmits the generated X-ray generation signal to the X-ray generating unit 102.

The power supply unit 111 includes a power source for supplying electric power to each unit in the X-ray imaging apparatus 101 such as the main control unit 110 and the X-ray generating unit 102. External power supply to the power supply unit 111 may be from a commercial power source of single phase 100 V or from a cigarette lighter socket in an automobile of a DC voltage of 12 V or 24 V. External power supply to the power supply unit 111 may be from a battery of a DC voltage such as a lithium ion battery, a nickel-metal hydride battery, or a fuel cell.

The power supply unit 111 boosts the voltage of externally supplied electric power to about 300 V, for example. The power supply unit 111 supplies the electric power of the boosted voltage to the high voltage generating unit provided in the X-ray generating unit 102.

Note that the control unit 103 is a computer including a central processing unit (CPU) and a random access memory (RAM) or a read-only memory (ROM). The CPU executes a computer program to thereby function as the X-ray control unit 107, the irradiation condition setting unit 108, the X-ray irradiation instructing unit 109, and the operation unit 119.

When the arm unit 105 is extended and the X-ray tube of the X-ray generating unit 102 is locked in a position above the image receiving surface of the X-ray image receiving unit 104, an extension recognition unit 120 transmits an extension recognition signal to the main control unit 110 in order to notify the main control unit 110 of completion of the extension processing. When the X-ray generating unit 102 is locked in a position that opposes the X-ray image receiving unit 104, an opposing recognition unit 121 transmits an opposing recognition signal to the main control unit 110 in order to notify the main control unit 110 of completion of the opposing processing. When the main control unit 110 receives the recognition signal from the X-ray image receiving unit recognition unit 112, the extension recognition signal from the extension recognition unit 120, and the opposing recognition signal from the opposing recognition unit 121, the main control unit 110 determines that X-ray irradiation is allowed. When the X-ray irradiation switch is pressed by an operation performed by an operator and the X-ray irradiation instruction signal is transmitted, the main control unit 110 generates the X-ray generation signal.

The main control unit 110 drives the lead blades using a motor or the like provided in the X-ray movable diaphragm 106 on the basis of the recognition signal received from the X-ray image receiving unit recognition unit 112 and automatically adjusts the irradiation range so that the irradiation range is in a predetermined range. Note that the recognition signal includes information on whether or not the X-ray image receiving unit 104 is housed and the kind (an FPD sensor, a CR cassette, or a film cassette), the size, and the mounting orientation of the X-ray image receiving unit 104.

In addition to the structure described above, the X-ray imaging apparatus 101 may be configured to further include a display unit 113, in the case where an FPD sensor is used as the X-ray image receiving unit 104, which displays an X-ray image received by the FPD sensor. Various types of display apparatuses such as a tablet-type multifunction portable terminal may be used as the display unit 113 and the display unit 113 may be provided separately from the X-ray imaging apparatus 101. Alternatively, the display unit 113 may be provided on the upper portion 151 of the arm unit 105, for example, on the outer surface thereof, opposite to the X-ray generating unit 102.

The arm unit 105 is a member for fixing the X-ray generating unit 102, the control unit 103, and the housing unit 115 in place. Note that, for convenience of description, the "upper" and "lower" sides of the arm unit 105 correspond to the "upper" and "lower" sides of the arm unit 105 illustrated in FIG. 3 unless otherwise noted.

The arm unit 105 is formed of rod-shaped members. The arm unit 105 extends in an arc shape in two steps, for example, and the "upper" side is an upper portion 151 and the "lower" side is a lower portion 152. One end of the lower portion 152 is fixed to the housing unit 115 with a hinge shaft, for example, and the control unit 103 is fixed between the rod-shaped members in the lower portion 152 in the exemplary embodiment. The X-ray generating unit 102 is fixed between the rod-shaped members in the upper portion 151. When the upper portion 151 of the arm unit 105 is extended, the X-ray generating unit 102 and the X-ray image receiving unit 104 are opposed to each other and an X-ray tube focal spot F of the X-ray generating unit 102 is positioned vertically above the center position of the image receiving surface of the X-ray image receiving unit 104. Note that the distance (distance C in FIG. 3) between the X-ray tube focal spot F of the X-ray generating unit 102 and the image receiving surface of the X-ray image receiving unit 104 that is housed in the housing unit 115 is preferably 1100 mm or less, taking into consideration portability. The space between the X-ray generating unit 102 and the X-ray image receiving unit 104 (for example, a region surrounded by the upper portion 151 and lower portion 152 of the arm unit 105 and the X-ray generating unit 102, hereinafter referred to as the "interior side") is in a shape formed by an arc portion and a base such that a subject H is capable of getting into the space.

Figure 4A:
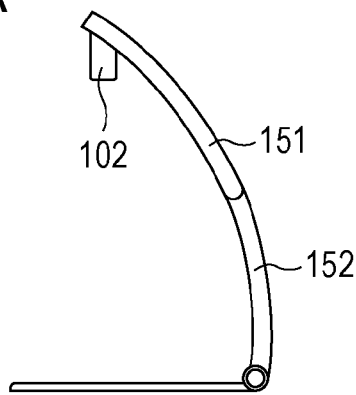
FIGS. 4A to 4F are diagrams schematically illustrating retraction and housing of an arm unit of the X-ray imaging apparatus.
Figure 4B:
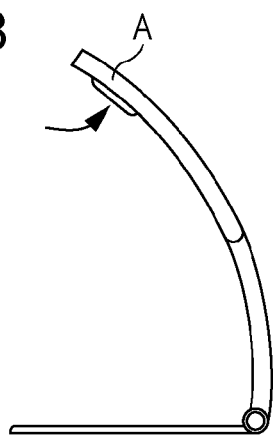
Figure 4C:
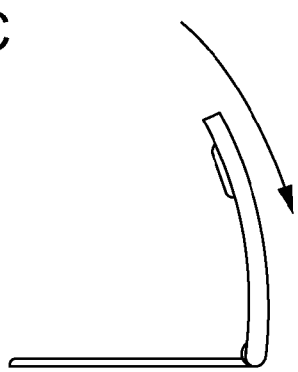
Figure 4D:
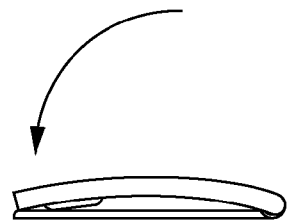

FIGS. 4A to 4F are diagrams schematically illustrating retraction and folding of the upper portion 151 (first arm portion) and lower portion 152 (second arm portion) of the arm unit 105 and the housing unit 115. In the case of housing and transportation, the X-ray generating unit 102 is capable of pivoting on a point A toward the upper portion 151 as illustrated in FIG. 4B. The upper portion 151 has a rail (not illustrated) in each of the left inner side face and the right inner side face thereof, the rail is formed in a C-shape or an angular C-shape in cross section, and the side face of the opening of the rail in the left inner side face and the side face of the opening of the rail in the right inner side face are disposed so as to face each other. The lower portion 152 has a projection on the side face thereof, which is fitted into the rail in the upper portion 151 and the upper portion 151 is capable of sliding on the lower portion 152 (retracting towards the housing unit) as illustrated in FIG. 4C. As a matter of course, the structure may be such that the lower portion 152 has a groove in the side face thereof and the upper portion 151 has a projection. A projection need not be used and the structure may be in a form such that a C-shaped or an angular C-shaped member is disposed around a rod-shaped member. The lower portion 152 has, on one end thereof (a proximal end), the hinge shaft that is joined to the housing unit 115 and is capable of pivoting on the hinge shaft. When folded, part of the arm unit 105 is in contact with part of the housing unit 115 and the hinge shaft and/or a contact portion of the arm unit 105 and the housing unit 115 serve as support points to thereby provide a function in which the retracted arc-shaped arm unit 105 protects the X-ray image receiving unit 104 against shock.

Figure 4E:
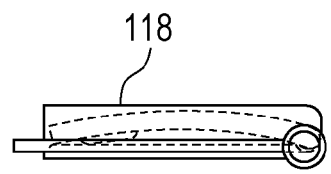
Figure 4F:
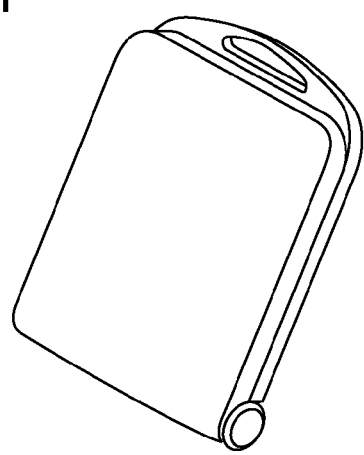

Furthermore, in the case of housing (for storage) or transportation, shock resistance and portability may be further improved by having the X-ray imaging apparatus 101 built into a housing case 118 having a pull handle and wheels as illustrated in FIGS. 4E and 4F.

That is, the X-ray imaging apparatus 101 includes the X-ray generating unit 102 that radiates X-rays, the housing unit 115 configured to house therein an X-ray image receiving unit 104 that detects X-rays, and the arm unit 105 that supports the X-ray generating unit 102. For storage and transportation, the arm unit 105 is foldable toward (or collapsible onto) the housing unit 115. For imaging operation, the arm unit 105 is pivotable away from the housing unit 115 and extends above the X-ray image receiving unit 104. Here it should be noted that, in certain arrangements, the X-ray image receiving unit 104 may be obviated from the basic structure of the X-ray imaging apparatus 101, as the housing unit 115 may be configured to house therein a variety of different X-ray image receiving units, such as a FPD, a film cassette, or the like, as described above.

Note that aluminum alloy, titanium, CFRP, or the like is used as a material of the arm unit 105. With such a structure, the weight of the arm unit 105 may be reduced and the rigidity thereof may be enhanced.

Next, an example of processing relating to the X-ray imaging apparatus 101 according to an exemplary embodiment is described with reference to FIG. 5. FIG. 5 is a flowchart illustrating an exemplary flow process relating to an imaging operation of the X-ray imaging apparatus 101. Processing instructions (e.g., an algorithm), except for manual operations and actions performed by an operator, is stored in a RAM or a ROM of a computer in the main control unit 110 as a computer program (computer software). A CPU of the computer in the control unit 103 reads and executes the computer program, so that processing is performed.

First, in step S101, the X-ray image receiving unit 104 is housed in the housing unit 115 by an operator or the like.

In step S102, the X-ray image receiving unit recognition unit 112 recognizes whether or not the X-ray image receiving unit 104 is properly housed in the housing unit 115, recognizes the type, size and orientation of the X-ray image receiving unit 104, generates a recognition signal, and transmits the generated recognition signal to the main control unit 110.

Note that, in the case where an FPD sensor is used as the X-ray image receiving unit 104, step S102 may be skipped as long as the FPD sensor is housed in the housing unit 115 in advance.

In step S103, the housing unit 115 and the lower portion 152 of the arm unit 105 of the X-ray imaging apparatus 101 is positioned near the subject H by an operator or the like, as shown in FIG. 3.

Note that step S101 and step S103 may be executed in reverse order. More specifically, the X-ray image receiving unit 104 may be inserted in the housing unit 115 after the housing unit 115 of the X-ray imaging apparatus 101 is inserted under the subject H.

In step S104, when an operation of extending the arm unit 105 is performed by an operator or the like and such an operation is completed, the extension recognition unit 120 transmits an extension completion signal to the main control unit 110.

In step S105, when an operation of arranging the X-ray generating unit 102 opposite the X-ray image receiving unit 104 is performed by an operator or the like and such an operation is completed, the opposing recognition unit 121 transmits an opposing completion signal to the main control unit 110.

In step S106, the irradiation condition setting unit 108 sets the X-ray irradiation conditions including an X-ray tube voltage, an X-ray tube current, X-ray irradiation time, and the like in accordance with an operation performed by an operator or the like on a touch panel or the like disposed in the exterior portion of the control unit 103. Note that the main control unit 110 is capable of setting the X-ray irradiation conditions on the basis of the recognition signal including information on the kind, size, and orientation of the X-ray image receiving unit 104, which has been received from the X-ray image receiving unit recognition unit 112 in step S102. Furthermore, the main control unit 110 is capable of automatically setting the X-ray irradiation conditions at recommended values or predetermined values.

In step S107, the X-ray movable diaphragm 106 receives an irradiation range signal generated by the main control unit 110. The X-ray movable diaphragm 106 drives the lead blades using a motor or the like on the basis of the irradiation range signal.

In step S108, when an operation such as pressing on the dead-man-type button is performed by an operator or the like, the X-ray irradiation instructing unit 109 transmits an X-ray irradiation instruction signal to the X-ray control unit 107. The X-ray control unit 107 receives an irradiation condition signal from the main control unit 110 and the X-ray irradiation instruction signal from the X-ray irradiation instructing unit 109. Then the X-ray control unit 107 transmits an X-ray generation signal to the X-ray generating unit 102 at the time when the conditions for X-ray irradiation are met. When the X-ray generating unit 102 receives the X-ray generation signal, the X-ray generating unit 102 radiates X-rays.

In step S109, after the X-ray generating unit 102 radiates X-rays, the X-ray imaging apparatus 101 displays a captured image on the display unit 113 (not illustrated). Accordingly, an operator or the like is capable of checking the captured X-ray image. Note that the method used for checking a captured X-ray image differs in accordance with the kind of the X-ray image receiving unit 104 used.

As described above, in the exemplary embodiment of the present invention, an operator houses the X-ray image receiving unit 104 in the housing unit 115 in advance in step S101 and the irradiation condition setting unit 108 sets the irradiation conditions in step S106. With such a scheme, X-rays may be radiated while an operator only has to insert the housing unit 115 of the X-ray imaging apparatus 101 under a subject H in step S103 and operate the X-ray irradiation instructing unit 109 in step S108. Furthermore, unnecessary irradiation and, when a CR cassette or a film cassette is used as the X-ray image receiving unit 104, double irradiation may be prevented. As a result, operability may be increased.

The present invention provides a technique effective for use with an X-ray imaging apparatus. With the present invention, installability, portability, and operability may be increased.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-279482 filed Dec. 21, 2012, which is hereby incorporated by reference herein in its entirety.

What is claimed is:

1. An X-ray imaging apparatus comprising:
   an X-ray generating unit configured to radiate X-rays;
   an X-ray image receiving unit configured to detect X-rays;
   an arm unit configured to support the X-ray generating unit and extend above the X-ray image receiving unit,
   wherein the arm unit has a mechanism that allows the arm unit to be folded so as to cover the X-ray image receiving unit; and
   an exterior unit configured to cover the X-ray generating unit, the X-ray image receiving unit and the arm unit in a folded state.

2. The X-ray imaging apparatus according to claim 1, wherein the arm unit extends such that an X-ray tube focal spot generated by the X-ray generating unit is positioned vertically above a center of an image receiving surface of the X-ray image receiving unit.

3. The X-ray imaging apparatus according to claim 1, wherein the arm unit extends in an arc shape.

4. The X-ray imaging apparatus according to claim 1, further comprising:
   a control unit configured to control the X-ray generating unit and the X-ray image receiving unit.

5. The X-ray imaging apparatus according to claim 4, wherein the exterior unit has a pull handle and wheels.

6. An X-ray imaging apparatus comprising:
   an X-ray generating unit configured to radiate X-rays;
   an X-ray image receiving unit configured to detect X-rays; and
   an arm unit having a distal end and configured to support at the distal end the X-ray generating unit and to be foldable toward an image receiving surface of the X-ray image receiving unit.

7. An X-ray imaging apparatus comprising:
   an X-ray generating unit configured to radiate X-rays;
   a housing unit configured to house therein an X-ray image receiving unit;
   a control unit configured to control the X-ray generating unit and the X-ray image receiving unit; and
   an arm unit having a proximal end and a distal end, and configured to support at the distal end thereof the X-ray generating unit and to connect at the proximal end thereof with the housing unit,
   wherein the arm unit extends away from the X-ray image receiving unit to position the X-ray generating unit for an imaging operation, and contracts towards the housing unit for a storage operation.

8. The X-ray imaging apparatus according to claim 7, wherein the housing unit and the arm unit are pivotably joined to each other, so that the arm unit and the housing unit are collapsible onto each other.

9. The X-ray imaging apparatus according to claim 7,
   wherein the arm unit includes an upper portion and a lower portion, and
   wherein the upper portion is configured to slide on the lower portion to retract the arm unit towards the housing unit.

\* \* \* \* \*